(12) United States Patent
Gordon

(10) Patent No.: US 9,198,738 B2
(45) Date of Patent: Dec. 1, 2015

(54) COMBINATION TONGUE AND FLAP RETRACTOR

(71) Applicant: Manuel Barry Gordon, New York, NY (US)

(72) Inventor: Manuel Barry Gordon, New York, NY (US)

(*) Notice: Subject to any disclaimer, the term of this patent is extended or adjusted under 35 U.S.C. 154(b) by 0 days.

(21) Appl. No.: 13/624,257

(22) Filed: Sep. 21, 2012

(65) Prior Publication Data

US 2013/0017509 A1    Jan. 17, 2013

Related U.S. Application Data

(63) Continuation of application No. 12/405,751, filed on Mar. 17, 2009, now Pat. No. 8,297,972.

(51) Int. Cl.
 *A61C 3/00* (2006.01)
 *A61B 13/00* (2006.01)
 *A61C 17/06* (2006.01)

(52) U.S. Cl.
 CPC . *A61C 3/00* (2013.01); *A61B 13/00* (2013.01); *A61C 17/043* (2013.01)

(58) Field of Classification Search
 CPC ....... A61B 13/00; A61B 1/24; A46B 15/0081
 USPC .............. 433/91–96, 29–31, 1, 3, 140–148; 600/237–242, 205, 210, 201, 213; 604/902; D24/136, 135, 139; 128/860, 128/200.15
 See application file for complete search history.

(56) References Cited

U.S. PATENT DOCUMENTS

| 637,970 | A | * | 11/1899 | Nyman | .......................... 433/93 |
| 1,009,551 | A | | 11/1911 | Nations | |
| 1,465,259 | A | | 10/1921 | Friedman | |
| 1,497,749 | A | | 5/1922 | Diack | |
| 2,603,870 | A | | 7/1952 | Harald | |

(Continued)

FOREIGN PATENT DOCUMENTS

CN        201091589 Y  *  7/2008

OTHER PUBLICATIONS

English language machine translation of CN201091589Y, Jul. 2008.*

(Continued)

*Primary Examiner* — Cris L Rodriguez
*Assistant Examiner* — Matthew Saunders
(74) *Attorney, Agent, or Firm* — Stroock & Stroock & Lavan LLP

(57) ABSTRACT

A combination refractor includes an operational unit, a neck region and a handle region. The operational unit further includes a tongue retractor and a flap retractor. The tongue retractor may be concave to provide for a natural area to encapsulate the tongue. The tongue and flap refractors may also be provided as part of a continuous planar extension of the operational unit or may be disposed on different planes. The flap retractor may be formed of a tapered extended edge or tab, which can be made in various lengths and include a beveled edge. A suction mechanism may be added for eliminating fluids. The neck region may contain an S-shaped bend or lateral bends for better operative functionality and ergonomics. The proximal end of the handle region, opposite the operational unit, may further include any useful apparatus, such as a periosteal elevator or periosteal retractor.

33 Claims, 20 Drawing Sheets

(56) References Cited

U.S. PATENT DOCUMENTS

| | | | |
|---|---|---|---|
| 2,723,661 A * | 11/1955 | Hull | 600/240 |
| 2,831,480 A | 4/1958 | Milano | |
| 3,090,122 A | 5/1963 | Erickson | |
| 3,863,627 A * | 2/1975 | Bouffard | 600/210 |
| D235,549 S * | 6/1975 | Funderburk | D24/135 |
| 4,270,902 A | 6/1981 | Wiland | |
| D291,001 S * | 7/1987 | Gaskins | D24/147 |
| 4,883,426 A | 11/1989 | Ferrer | |
| 5,078,602 A | 1/1992 | Honoshofsky | |
| D391,370 S * | 2/1998 | Cho | D24/147 |
| 5,730,597 A | 3/1998 | Luttrell | |
| 5,816,806 A | 10/1998 | Herbst et al. | |
| 5,846,192 A | 12/1998 | Teixido | |
| 6,045,499 A * | 4/2000 | Pitesky | 600/240 |
| 6,174,162 B1 * | 1/2001 | Pozzi | 433/3 |
| 6,241,658 B1 | 6/2001 | Goodrich | |
| 6,575,749 B1 | 6/2003 | Greenwald | |
| D509,590 S * | 9/2005 | Cho | D24/147 |
| 7,238,023 B1 | 7/2007 | Enos | |
| 2001/0034474 A1 * | 10/2001 | Ryan | 600/240 |
| 2002/0128673 A1 | 9/2002 | Ripich et al. | |
| 2004/0086828 A1 | 5/2004 | Torres | |
| 2005/0197665 A1 * | 9/2005 | Teed et al. | 606/161 |
| 2005/0228233 A1 | 10/2005 | Ritland | |
| 2010/0021863 A1 * | 1/2010 | Braman | 433/140 |
| 2010/0240005 A1 | 9/2010 | Gordon et al. | |

OTHER PUBLICATIONS

Instruments—Miscellaneous, Knives/Spatulas/Retractors, Sullivan-Schein Dental Supply Catalog, 2007, p. 584.
Instruments—Retractors, Misch Spoon and Minesota Retractor, Salvin Dental Supply Catalog, 2011, p. 114.
International Search Report and Written Opinion of the International Searching Authority for PCT/US2014/37077 mailed on Sep. 26, 2014.

* cited by examiner

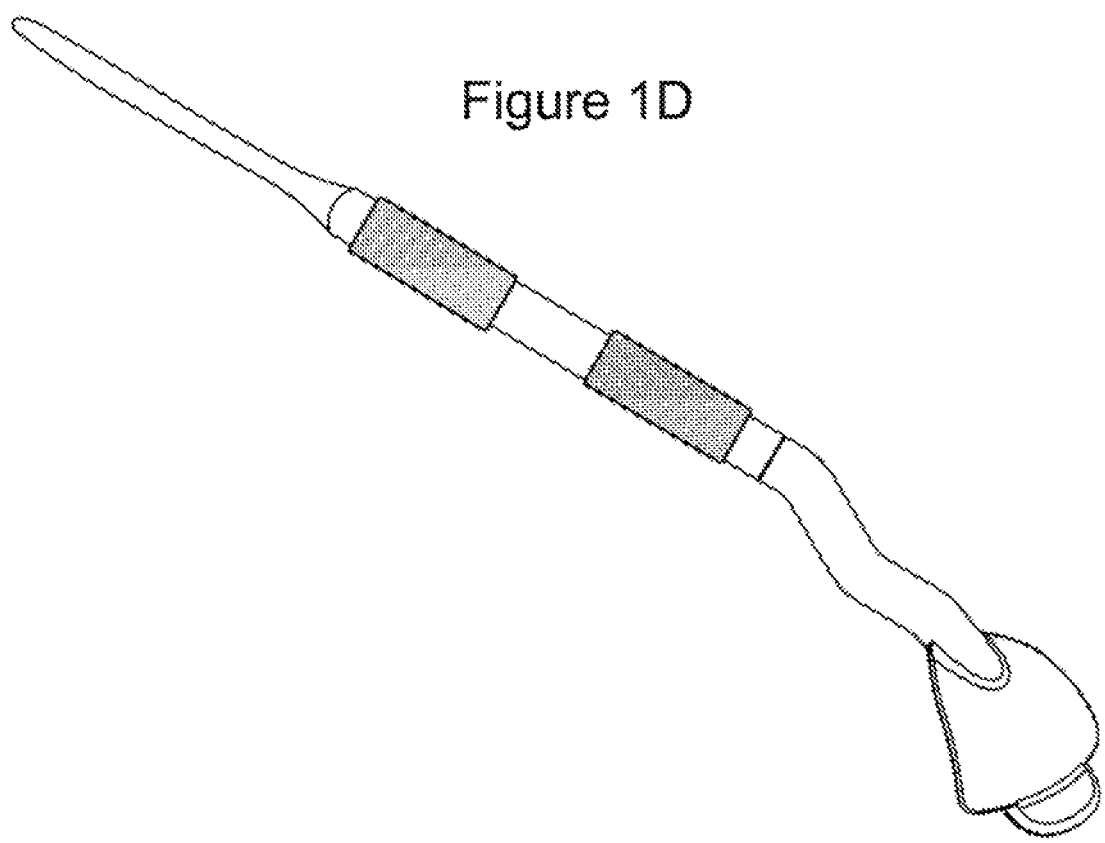
Figure 1D
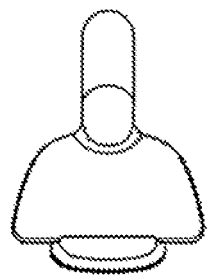 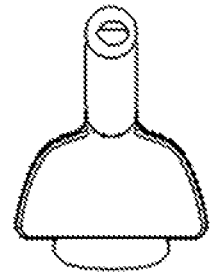
Figure 1E    Figure 1F

410

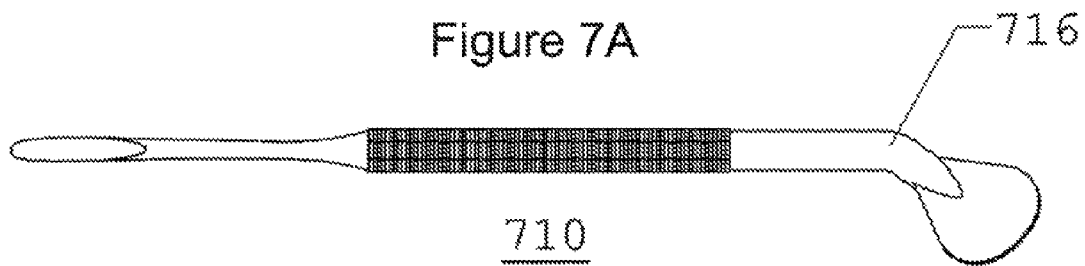
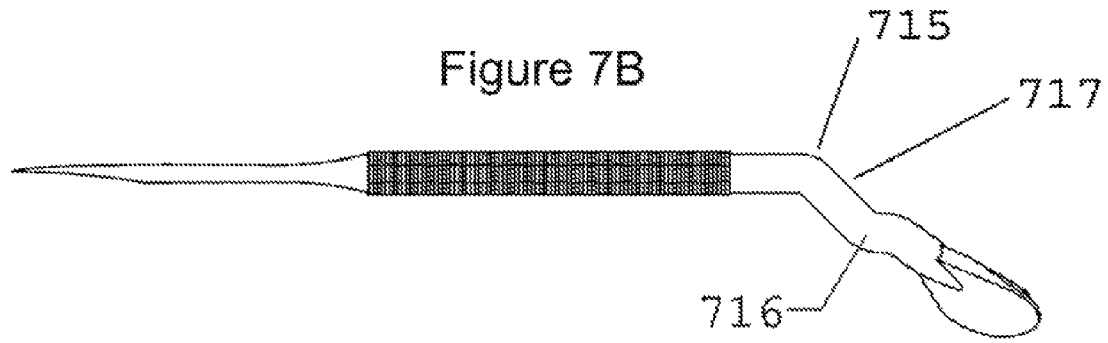
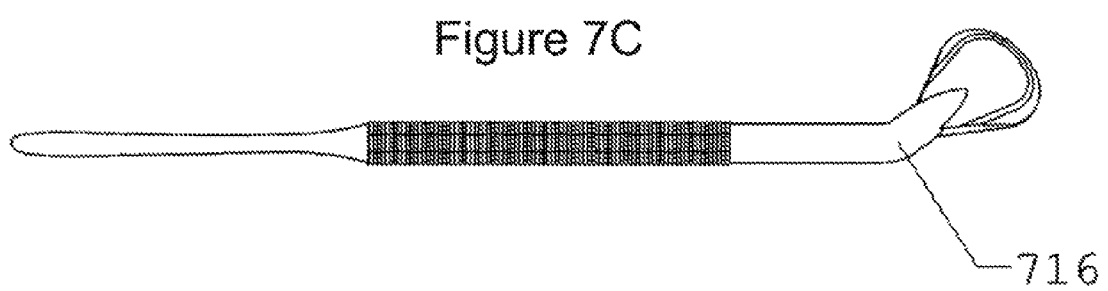

910

914

914

COMBINATION TONGUE AND FLAP RETRACTOR

CROSS-REFERENCE TO RELATED APPLICATIONS

This application is a continuation-in-part of U.S. application Ser. No. 12/405,751, filed on Mar. 17, 2009, now U.S. Pat. No. 8,297,972, the contents of which are incorporated herein by reference.

FIELD OF THE INVENTION

The present invention generally relates to the fields of general dentistry, oral surgery and periodontal surgery and to surgical instrumentation used therein. More specifically, the invention relates to a combination tongue and flap retractor and a distinct tongue retractor for use in general dental procedures, periodontal and oral surgery.

BACKGROUND OF THE INVENTION

Many dental procedures require the precise use of surgical instruments within a small and restricted area of operation. Furthermore, it is usually desirable to selectively supply air or water to a treatment area, drill in a treatment area, or to manipulate soft tissue. To do so, practitioners have conventionally used various instruments to manipulate tissue, suction liquids or retract the tongue while performing the desired procedure.

Conventional methods, however, present several problems. First, because of the restricted area, it is undesirable and usually impractical to crowd the oral cavity with multiple instruments. When two or three different instruments are placed in a patient's oral cavity, the practitioner is unable to clearly see the area of operation. Furthermore, because of the tight quarters, the instruments become limited in their range of motion. Thus, the degree of difficulty is unnecessarily increased for even the simplest of procedures.

Furthermore, the use of multiple instruments is impractical as it severely limits the ability of the dentist, periodontist, oral surgeon or assistant (herein, "Dentist") to properly perform the required procedures. For instance if a Dentist uses one hand to retract the tongue and another to hold a surgical flap away from the treatment area, then he will need to ask for an assistant to reach for another instrument, or the assistant must hold an instrument and retract either the tongue or flap while he/she is simultaneously suctioning or performing a different task. The only other option would be to perform the operation in segments or go back and forth between instruments until the procedure is complete. This unnecessary complexity lengthens the time of operation, reduces the efficiency of the procedure and increases patient discomfort.

Finally, a common problem in the field is that dentists regularly complain of neck, back, shoulder pain and carpal tunnel syndrome related hand pain. In fact, a comprehensive literature search indicates dental care providers are at 15 high risk for suffering a workplace musculoskeletal disorder (WMSD) and neuromuscular disorders, e.g. disc herniation. Studies have reported that dental workers who suffer a WMSD injury have a lost work day average of 93 days per incident. In fact, sixty-two percent of dental hygienists have complained of neck problems and eighty-one percent have complained of shoulder pain in one or both shoulders. Studies have also shown that between six and seven percent of all dental hygienists report being diagnosed with carpal tunnel syndrome and that fifty-nine percent of dentists have reported musculoskeletal pain. A survey of a U.S. Army dental clinic reported that over seventy-five percent of all dental workers complained of one or more carpal tunnel syndrome symptoms, over fifty percent complained of back and shoulder pain, and eleven percent were diagnosed as having carpal tunnel syndrome. These disorders and others can be addressed with proper emphasis on ergonomics and posture, and by shortening the length of the dental procedure.

Thus, missing from the art is an invention that allows greater control, while affording the Dentist an opportunity to practice with better posture. Moreover, an invention that reduces the time of operation would have several benefits for both patients and practitioners: (i) reducing the strain on the neck, back, shoulders and hands of Dentists, (ii) reducing the amount of discomfort experienced by patients during procedures in which they remain awake, and (iii) reducing the adverse risks to the patient associated with the use of general anesthesia in situations where patients are put to sleep for a procedure.

SUMMARY OF THE INVENTION

The present invention, in one embodiment, is directed to a combination tongue and surgical flap retractor. The combination retractor may include an operational unit, a neck region and a handle region. The operational unit further includes a tongue retractor and a flap retractor. The tongue retractor may be formed with a concave shape or with an increased overall thickness of the operational unit. The flap retractor may be formed with a tapered extended edge or tab, which can be made in various lengths. Furthermore, the flap retractor may also include a beveled edge. The combination retractor may be formed in a way such that the tongue refractor is disposed on a different plane than the flap retractor. The retractor may also include a suction mechanism for eliminating fluids such as saliva, water, and blood from the oral cavity.

The present invention is also directed to improved ergonomics in the neck region of the combination retractor, the non-combination tongue retractor and in the suction device embodiments. In one embodiment, the neck region contains an S-shaped design for better ergonomics. Furthermore, the neck region may also include a lateral bend positioned at the proximal end of the operational unit, so as to position the operational unit either to the right or the left with respect to the central axis of the handle. Therefore, this facilitates specific use on a respective side of the mouth based on the direction of the lateral bend.

Finally, the present invention is directed to improvements in the handle region of the combination retractor. In one embodiment, the handle region includes a grip portion. The proximal end of the handle region may further include a dental pick, a dental probe, a dental hook, a periosteal elevator, or a periosteal retractor or any other dental instrument.

Other features and advantages of the present invention will become more fully apparent and understood with reference to the following description, the accompanying drawings and the appended claims.

BRIEF DESCRIPTION OF THE DRAWINGS

These and other objects and features of the invention will become more apparent by referring to the drawings, in which:

FIG. 1b is a side elevation view of the combination retractor shown in FIG. 1a;

FIG. 1c is a top view of the combination refractor shown in FIG. 1a;

FIG. 1d is a perspective view of the combination retractor shown in FIG. 1a;

FIG. 1e is a top plan view of the operational unit of the combination retractor shown in FIG. 1a;

FIG. 1f is a bottom plan view of the operational unit of the combination retractor shown in FIG. 1a;

FIG. 2b is a side elevation view of the combination retractor shown in FIG. 2a;

FIG. 2c is a top view of the combination refractor shown in FIG. 2a;

FIG. 2d is a perspective view of the combination retractor shown in FIG. 2a;

FIG. 2e is a top plan view of the operational unit of the combination retractor shown in FIG. 2a;

FIG. 2f is a bottom plan view of the operational unit of the combination retractor shown in FIG. 2a;

FIG. 3b is a side elevation view of the combination retractor shown in FIG. 3a;

FIG. 3c is a top view of the retractor shown in FIG. 3a;

FIG. 3d is a perspective view of the combination retractor shown in FIG. 3a;

FIG. 3e is a top plan view of the operational unit of the combination retractor shown in FIG. 3a;

FIG. 3f is a bottom plan view of the operational unit of the combination retractor shown in FIG. 3a;

FIG. 4b is a side elevation view of the combination retractor shown in FIG. 4a;

FIG. 4c is a top view of the combination refractor shown in FIG. 4a;

FIG. 4d is a perspective view of the combination retractor shown in FIG. 4a;

FIG. 4e is a top plan view of the operational unit of the combination retractor shown in FIG. 4a;

FIG. 4f is a bottom plan view of the operational unit of the combination retractor shown in FIG. 4a;

FIG. 5b is a side elevation view of the combination retractor shown in FIG. 5a;

FIG. 5c is a top view of the combination refractor shown in FIG. 5a;

FIG. 5d is a perspective view of the combination retractor shown in FIG. 5a;

FIG. 5e is a top plan view of the operational unit of the combination retractor shown in FIG. 5a;

FIG. 5f is a bottom plan view of the operational unit of the combination retractor shown in FIG. 5a;

FIG. 6b is a side elevation view of the combination retractor shown in FIG. 6a;

FIG. 6c is a top view of the combination refractor shown in FIG. 6a;

FIG. 6d is a perspective view of the combination retractor shown in FIG. 6a;

FIG. 6e is a top plan view of the operational unit of the combination retractor shown in FIG. 6a;

FIG. 6f is a bottom plan view of the operational unit of the combination retractor shown in FIG. 6a;

FIG. 7a is a bottom elevation view of a combination tongue and flap retractor with an S-shaped bend, bent to the left and thickened tongue and flap retractor both formed as a continuous planar extension in accordance with an embodiment of the present invention;

FIG. 7b is a side elevation view of the combination retractor shown in FIG. 7a;

FIG. 7c is a top view of the combination refractor shown in FIG. 7a;

FIG. 7d is a perspective view of the combination retractor shown in FIG. 7a;

FIG. 7e is a top plan view of the operational unit of the combination retractor shown in FIG. 7a;

FIG. 7f is a bottom plan view of the operational unit of the combination retractor shown in FIG. 7a;

FIG. 8b is a side elevation view of the combination retractor shown in FIG. 8a;

FIG. 8c is a top view of the combination refractor shown in FIG. 8a;

FIG. 8d is a perspective view of the combination retractor shown in FIG. 8a;

FIG. 8e is a top plan view of the operational unit of the combination retractor shown in FIG. 8a;

FIG. 8f is a bottom plan view of the operational unit of the combination retractor shown in FIG. 8a;

FIG. 9b is a side elevation view of the combination retractor shown in FIG. 9a;

FIG. 9c is a top view of the combination refractor shown in FIG. 9a;

FIG. 9d is a perspective view of the combination retractor shown in FIG. 9a;

FIG. 9e is a top plan view of the operational unit of the combination retractor shown in FIG. 9a;

FIG. 9f is a bottom plan view of the operational unit of the combination retractor shown in FIG. 9a;

FIG. 10b is a side elevation view of the combination retractor shown in FIG. 10a;

FIG. 10c is a top view of the combination retractor shown in FIG. 10a;

FIG. 10d is a perspective view of the combination retractor shown in FIG. 10a;

FIG. 10e is a top plan view of the operational unit of the combination retractor shown in FIG. 10a; and FIG. 10f is a bottom plan view of the operational unit of the combination retractor shown in FIG. 10a.

DETAILED DESCRIPTION OF ILLUSTRATIVE EMBODIMENTS

Figure 1A:
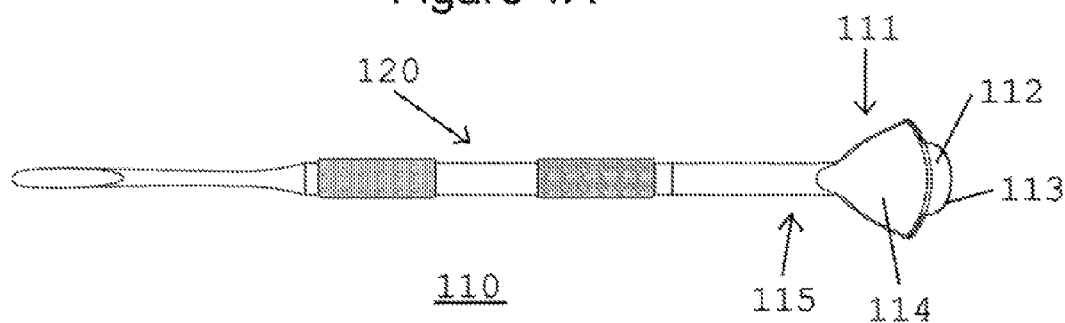
FIG. 1a is a bottom elevation view of a combination tongue and flap retractor with an S-shaped bend in accordance with an embodiment of the present invention.

Referring now to the drawings, FIG. 1a shows a combination tongue and flap retractor 110 according to one embodiment of the present invention. The combination retractor 110 may be formed of stainless steel, carbide, plastic or resin, or any other alloy or combination as is known in the art, and may include an operational unit 111, a neck region 115 and a handle region 120. Furthermore, the combination refractor may also be disposable.

The combination tongue and flap retractor may be formed so as to be hollow or solid in construction. Additionally, the retractor may be partially hollow and/or partially solid in construction, i.e., some portions of the retractor may be hollow and some portions may be solid. Additionally, the cross section of the various portions of the combination tongue and flap retractor may be in different shapes. For example, the retractor may be round in cross section, or it could be faceted, such as for example a six-sided hexagon, an eight-sided octagon, and the like. Additionally, portions of the retractor may have different cross sections. For example, one portion of the retractor may be round in cross section, while another portion of the retractor may be faceted.

The operational unit 111 may further include a flap refractor 112 at the distal end of the instrument. This flap retractor 112 preferably has a beveled 10 edge 113, which allows the flap retractor 112 to more easily hold the flap away from the treatment area. The operational unit 111 may further contain a concave tongue retractor 114 for retracting the tongue away from the treatment area where the Dentist is working. The concave tongue retractor 114 is used to retract and/or isolate the tongue during a procedure. The tongue retractor 114 differs from conventional instruments in terms of functional shape and size. As can be appreciated from FIG. 1b, the concave tongue retractor 114 is preferably shaped to provide for a natural area to encapsulate the tongue, thereby removing it from the treatment area.

Thus, the design of the flap retractor 112 makes it useful for reflecting a soft tissue flap (the gingival and/or gingival mucosa that has been raised as a surgical flap on the lingual aspect of the mandible). The combination retractor 110 may be used to perform both functions at once or perform each function, e.g., tongue retraction and flap retraction, either simultaneously or separately depending on the Dentist's need. Combining these functions into a single device eliminates the need for two separate devices in the oral cavity during procedures, frees up a hand of the Dentist for other potential uses or eliminates the need to have an assistant's hand in the treatment area, and shortens the time of operation.

The present invention provides improved ergonomics through the use of S-shapes and bends, which allow the instruments to be used on different sides of the mandible. These ergonomic features can be optionally incorporated into each of the devices discussed herein. In one embodiment, the neck region 115 may contain an S-shape bend 117. The S-shape allows the device to align more optimally in the oral cavity, such that a greatly reduced amount of downward and/or lateral force is needed to effect the desired tongue or flap retraction as compared to conventional instruments. This dramatically decreases the Dentist's fatigue and discomfort, and avoids prolonged strain on the neck, shoulder, back, and hand, thus reducing the risk of injury to the Dentist.

Figure 1B:
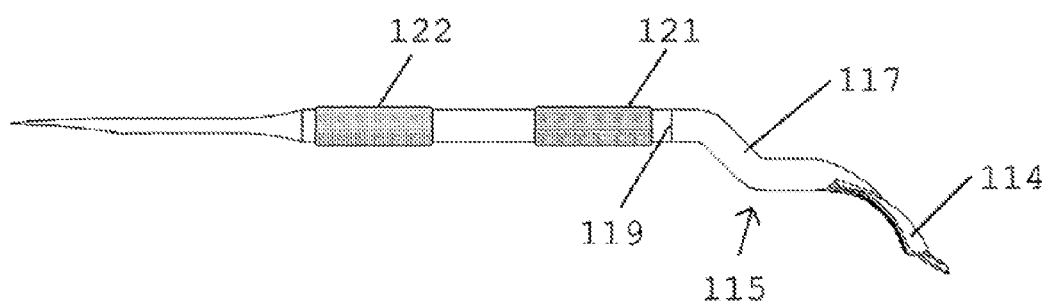

As illustrated in FIG. 1b, the neck region 115 of the combination tongue and flap retractor of the present invention may further include a thread 119 for connecting the retractor to the handle 120. The thread 119, located at the end of the neck region 115, serves to connect the neck region to the handle region 120. Additionally, any other method used in the art may be used for connecting the two places. Alternatively, the combination tongue and flap retractor may also be formed as a unitary, one-piece implement in which case threads or other attachment mechanisms would not be needed.

Figure 1C:
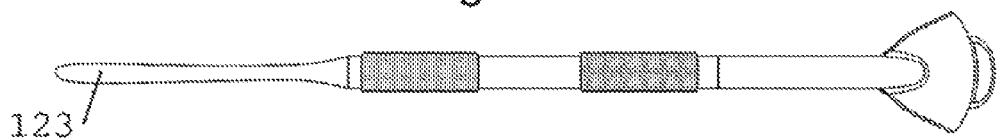

In one embodiment, the handle 120 may include grip portions 121 and 122. These grip portions provide the practitioner with a comfortable, yet sure grip as he manipulates the instrument. The grip portions 121 and 122 may be located at various positions along the handle 120 as desired for a comfortable grip. Further, the grip portions may be discrete, separate grip portions, or alternatively, a single grip portion may be provided on the retractor. In one embodiment the grip portions 121 and 122 may be constructed with an embossed pattern. This embossing may be in the form of ribs, raised dots, or the like, or may also be constructed of a separate grip mat made of plastic, rubber or any other suitable material. As shown in FIG. 1c, in one embodiment the proximal end of the handle may optionally include another dental instrument, such as a periosteal elevator 123. Furthermore, as can be appreciated by those skilled in the art, the proximal end of the handle 120 may instead include a dental probe, a dental hook, or other useful apparatus.

In another embodiment the tongue portion of the combination refractor may be longer and more sharply curved, i.e., having a curved profile. This embodiment, shown in FIGS. 2a-2f, has a tongue retractor 214 with an increased concavity (see FIG. 2b) for better encapsulation of the tongue and/or better accommodation of patients with larger tongues. The concave tongue and flap retractor 210 may be formed by sharply curving the distal portion of the tongue retractor 214, such that when viewed from the side, the tongue retractor 214 is substantially nonlinear and curved in profile.

Figure 2A:
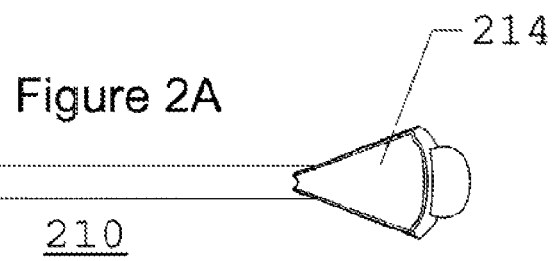
FIG. 2a is a bottom elevation view of a combination tongue and flap retractor with an S-shaped bend, where the flap retractor is at a reduced angle with respect to the handle axis and a more sharply curved tongue retractor in accordance with an embodiment of the present invention.
Figure 2B:
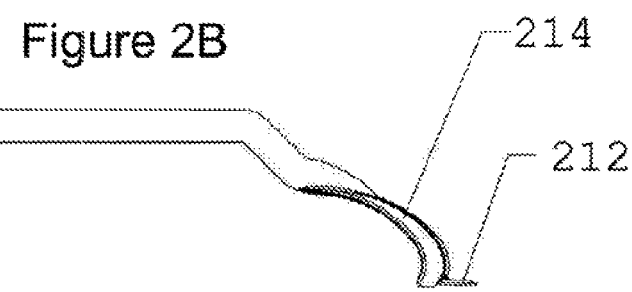
Figure 2C:
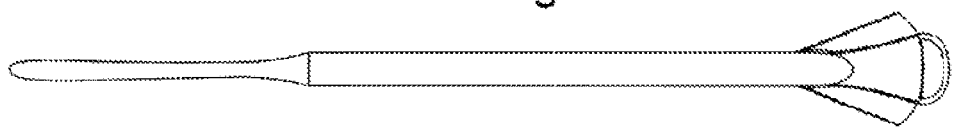
Figure 2D:
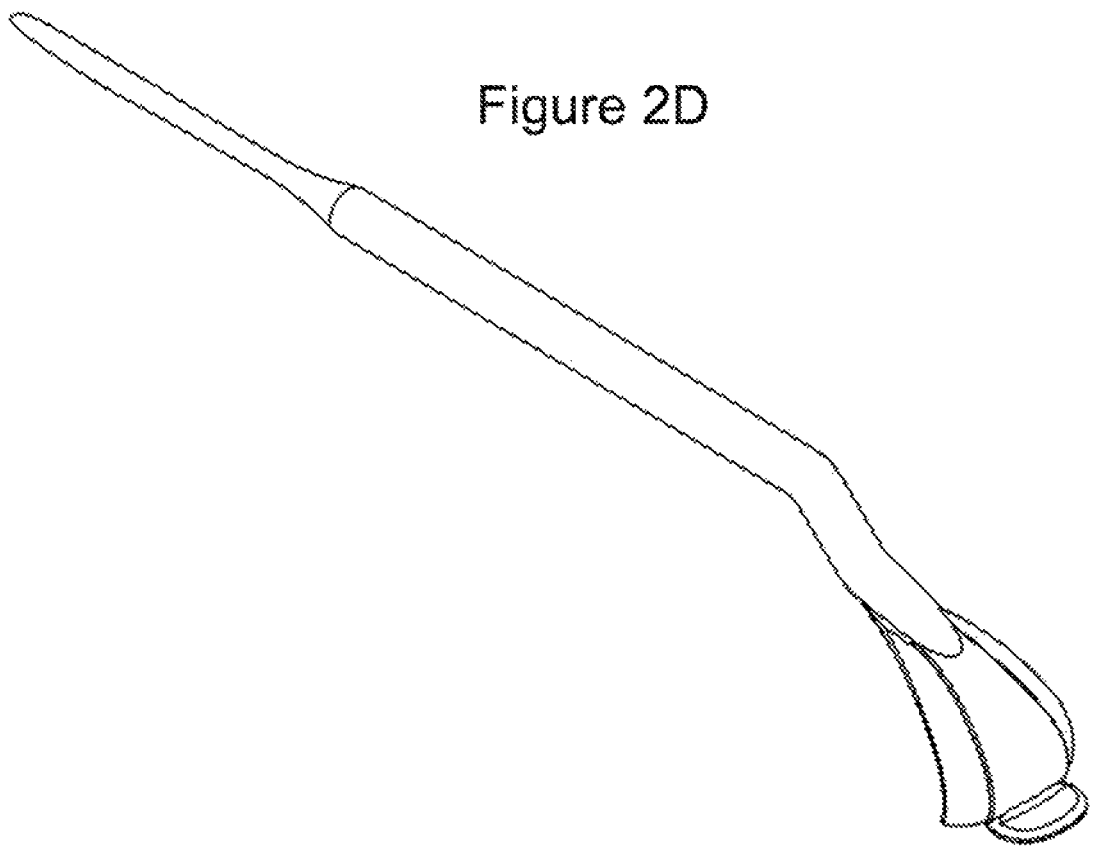
Figure 2E:
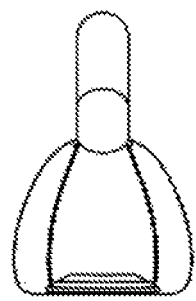
Figure 2F:
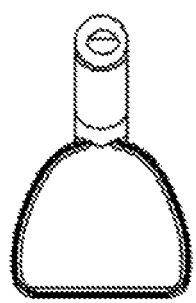
Figure 3A:
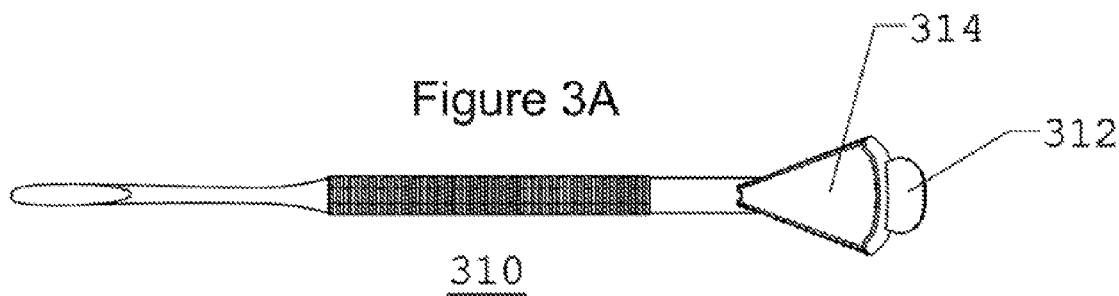
FIG. 3a is a bottom elevation view of a combination tongue and flap retractor with an S-shaped bend where the flap retractor is at a greater angle with respect to the handle axis, and a concave tongue retractor in accordance with an embodiment of the present invention.
Figure 3B:
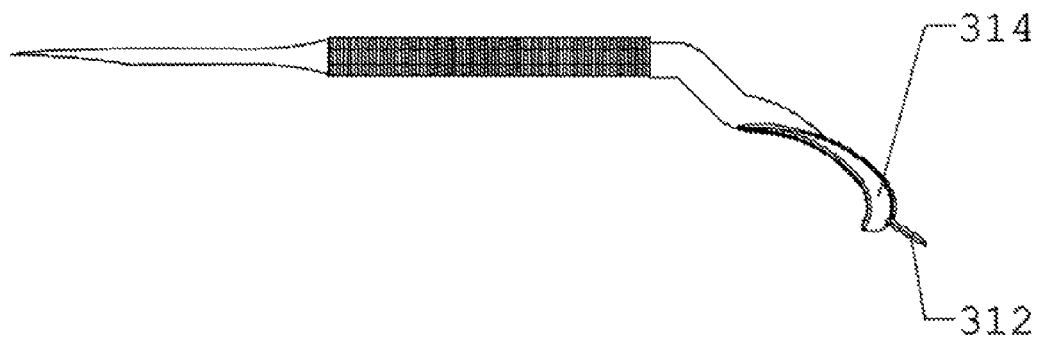
Figure 3C:
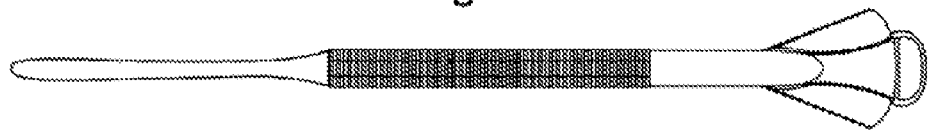
Figure 3D:
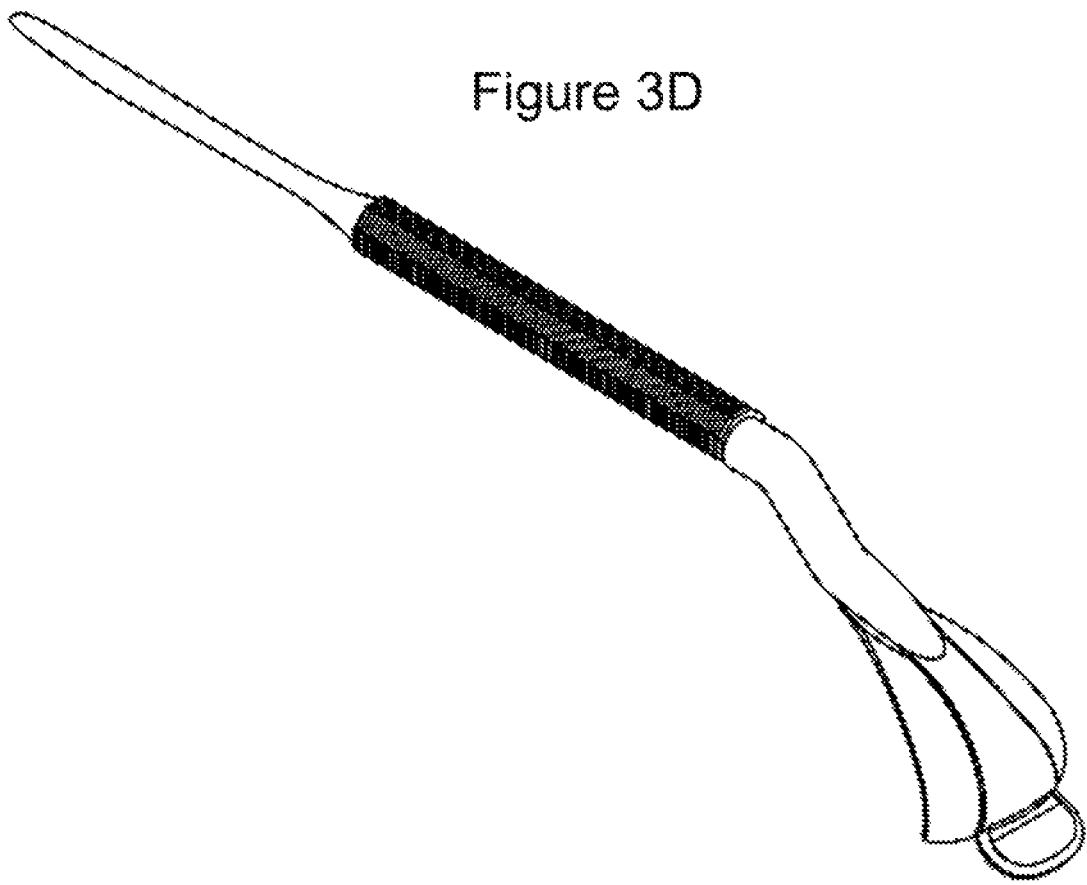
Figure 3E:
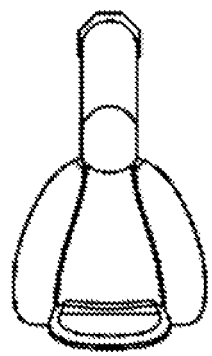
Figure 3F:
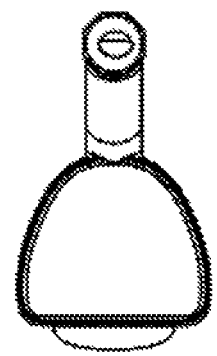

FIG. 3a shows another embodiment 310 in which the tongue retractor 314 may be located on a different plane than the flap retractor. As can be appreciated by comparing FIGS. 2b and 3b, the angle of the flap retractor may be varied with respect to the central axis of the handle. While the flap retractor 212 of FIG. 2b is disposed at a relatively shallow angle with respect to the central axis of the handle, the flap retractor 312 of FIG. 3b is disposed at a steeper angle. In general, this angle may range from zero degrees to almost 90 degrees. Moreover, the tongue retractor may also have the flap retractor positioned in generally the same plane as the tongue retractor.

Figure 4A:
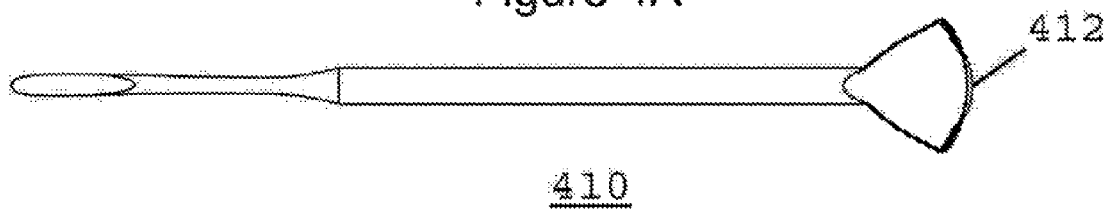
FIG. 4a is a bottom elevation view of a combination tongue and flap retractor with the tongue and flap refractor disposed on the same plane, with an S-shaped bend, and a short flap retractor in accordance with an embodiment of the present invention.
Figure 4B:
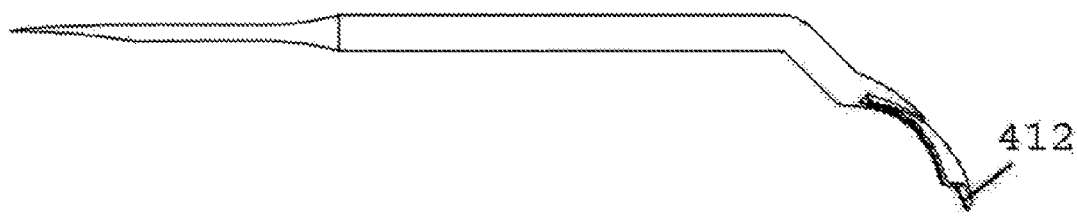
Figure 4C:
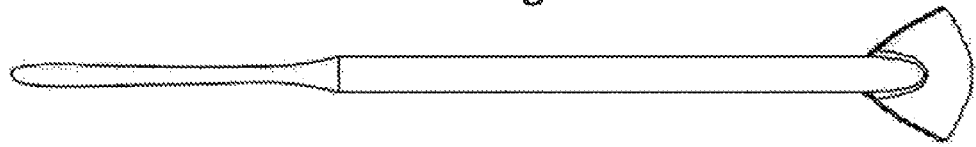
Figure 4D:
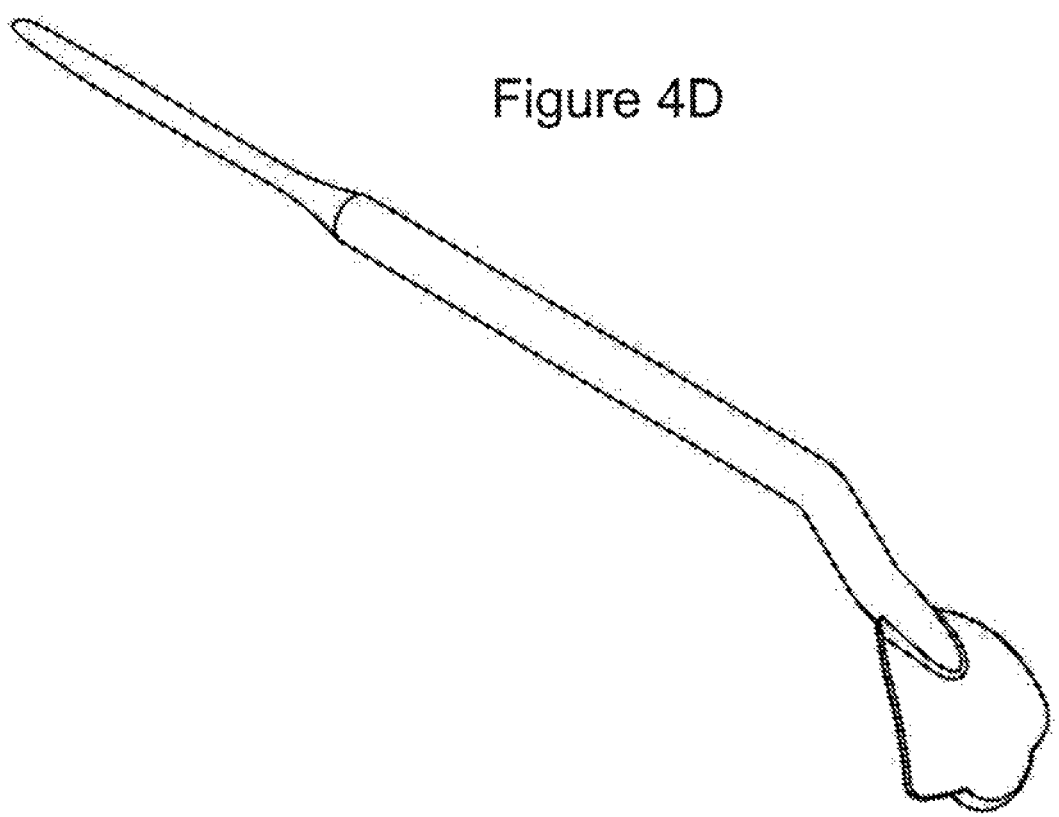
Figure 4E:
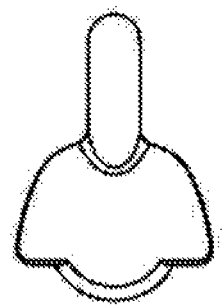
Figure 4F:
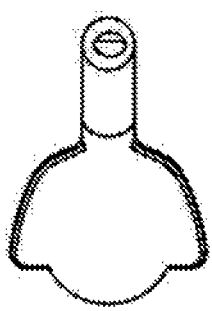

Thus, in one embodiment of the present invention, the concave tongue retractor and the flap retractor are integrated into a single instrument, a combination tongue and flap refractor. In addition, the flap refractor is in the form of a tapered, extended edge or tab, which can be made in various lengths. By way of illustration, FIG. 4a illustrates a concave tongue and flap retractor 410, similar to that of FIG. 1a, except that it includes a shortened flap retractor 412 as compared to flap retractor 112. The shortened flap retractor 412 may be useful when the flap being manipulated is not a large one.

Figure 5A:
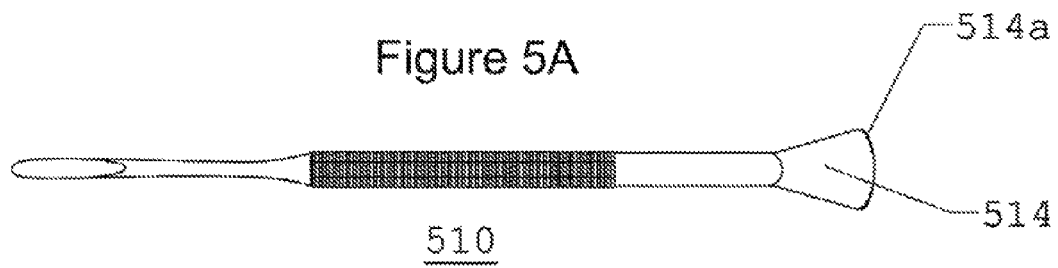
FIG. 5a is a bottom elevation view of a combination tongue and flap retractor with an S-shaped bend, and a thickened tongue and flap retractor both formed as a continuous planar extension in accordance with an embodiment of the present invention.
Figure 5B:
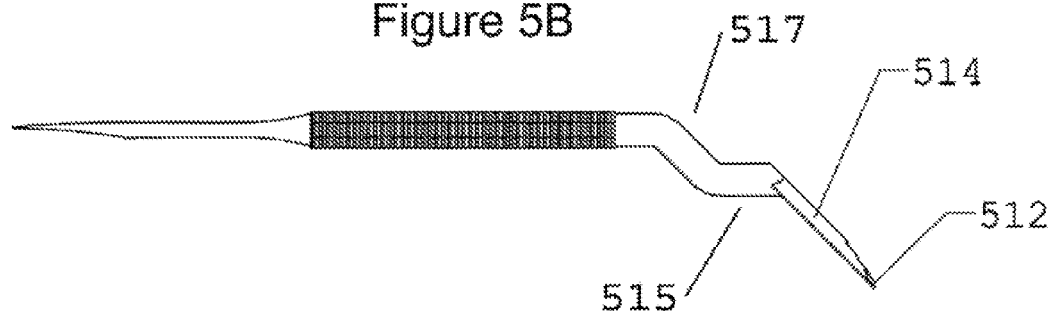
Figure 5C:
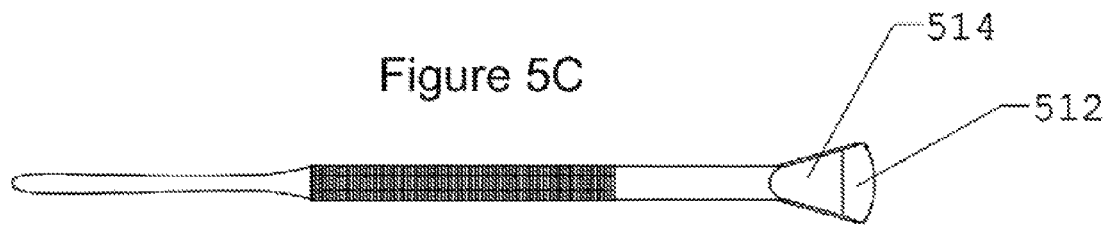
Figure 5D:
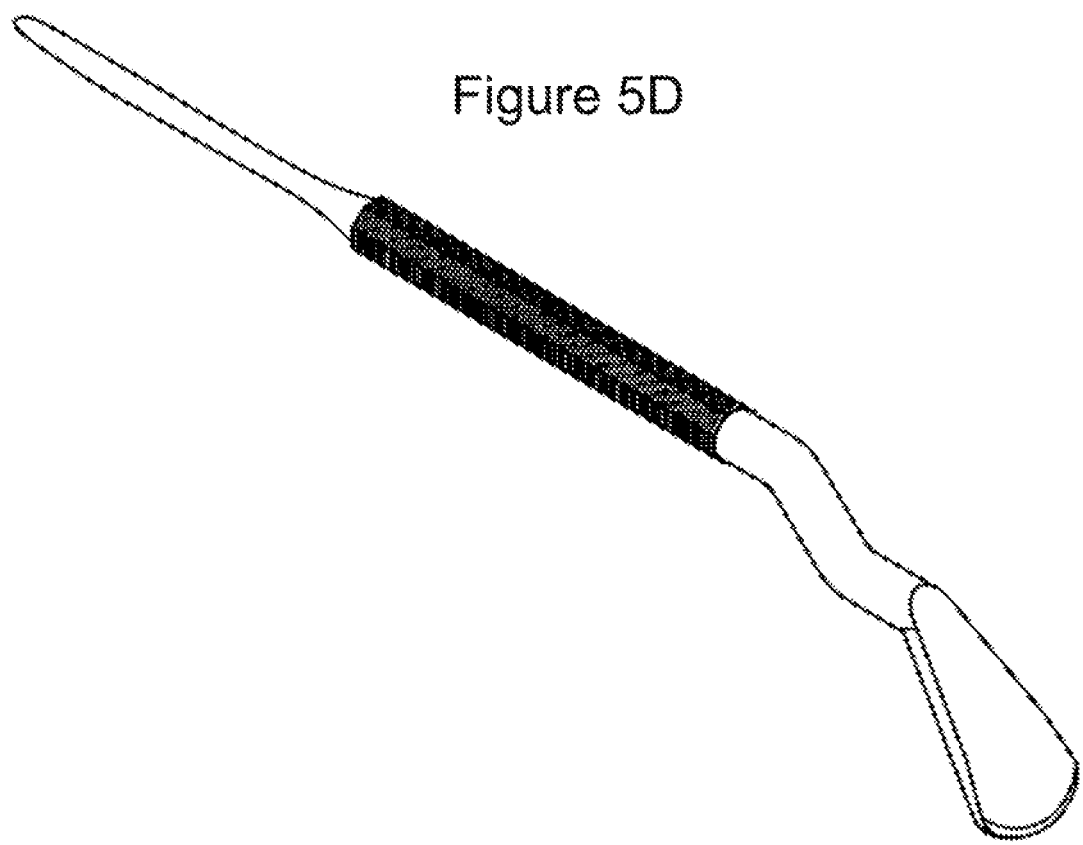
Figure 5E:
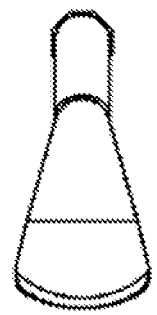
Figure 5F:
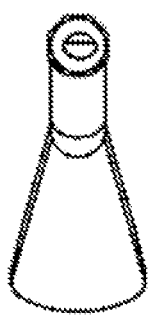

Yet another embodiment of the present invention is directed to an integrated non-concave tongue and flap retractor as shown in FIG. 5a. This combination tongue and flap retractor provides the same advantages as the combination tongue and flap retractor of the previous embodiments discussed above, but provides yet another option for the Dentist. Instead of the concave tongue retractor described above, the flap and tongue retractor 510 is provided with a greater thickness 514 relative to standard dental instruments, and is intended to be inserted into the oral cavity where the flap retraction is provided by a tapered leading edge 512 of the retractor 514. This device also incorporates specifically rounded corners 514a to better fit into the rounded shape of the mandible. The increased thickness portion 514 may be as little as a few tenths of a millimeter in thickness to several millimeters or more. For example, the thickness can be at least 0.5 millimeters. The integrated non-concave tongue and flap retractor 510 also includes the S-shaped bend 517 in the neck region 515 for better ergonomics and advantages as described herein.

Figure 6A:
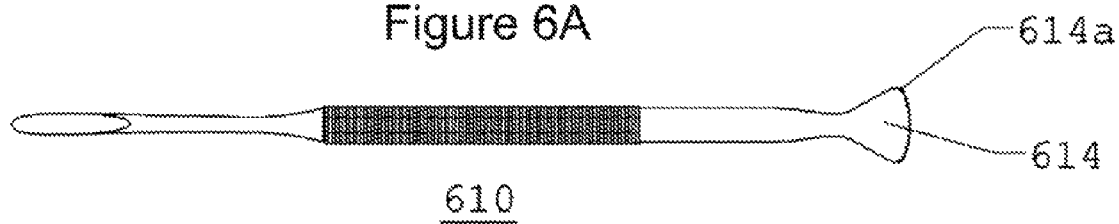
FIG. 6a is a bottom elevation view of a combination tongue and flap retractor with an S-shaped bend, and a small, thin tongue and flap retractor both formed as a continuous planar extension in accordance with an embodiment of the present invention.
Figure 6B:
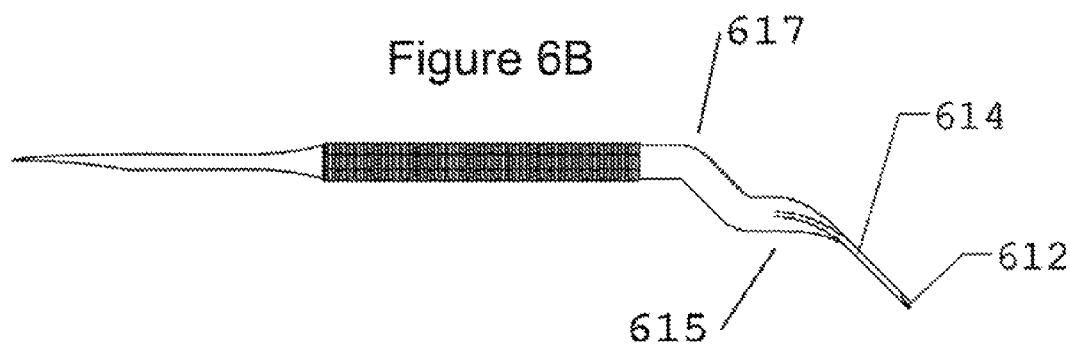
Figure 6C:
Figure 6D:
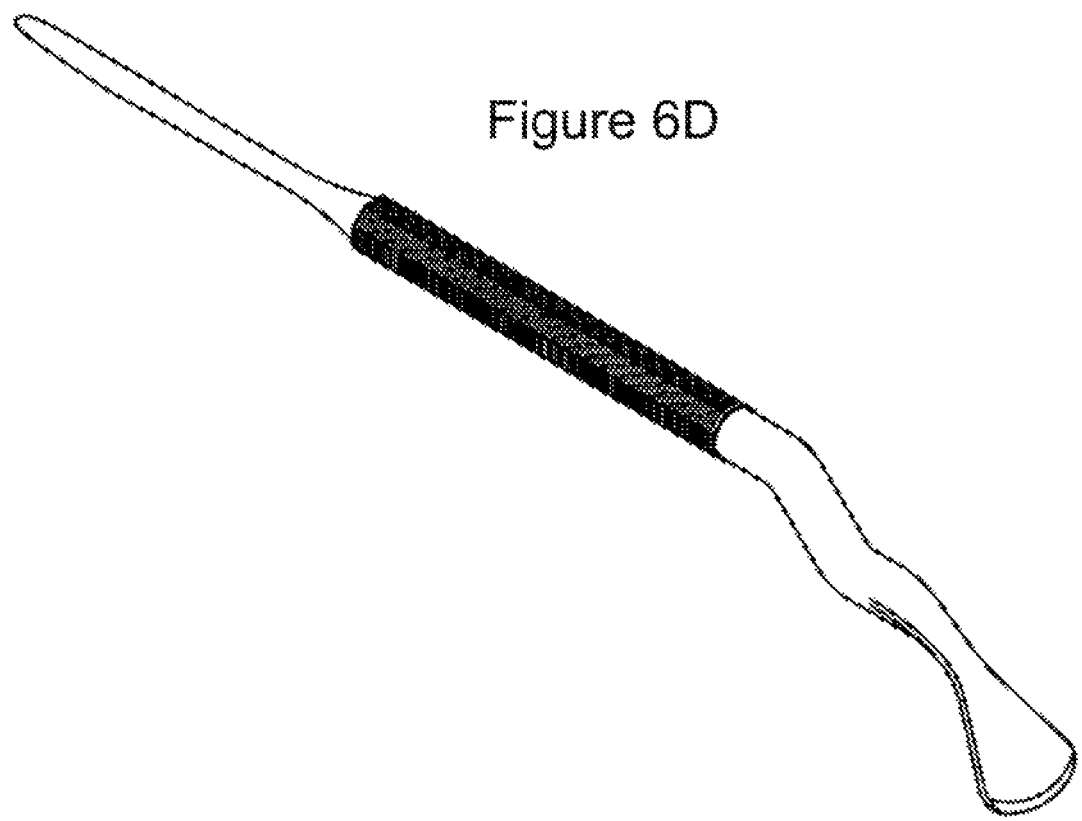
Figure 6E:
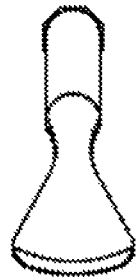
Figure 6F:
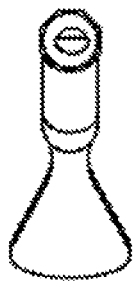

As can be further appreciated from FIG. 6a, the integrated non-concave tongue and flap retractor may be formed in various sizes. FIG. 6a, for example, shows an integrated retractor 610, similar to that of FIG. 5a but smaller in size. Similar to the embodiment of FIG. 5a, the integrated retractor includes rounded corners 614a to better fit in the mandible and also includes the S-shaped bend 617 in the neck region 615 for better ergonomics and advantages as described herein. The integrated retractor 610, also includes a greater thickness 614 and a tapered leading edge 612 similar to that of FIG. 5a. The increased thickness portion 614 may be as little as a few tenths of a millimeter in thickness to several millimeters of more.

Figure 7D:
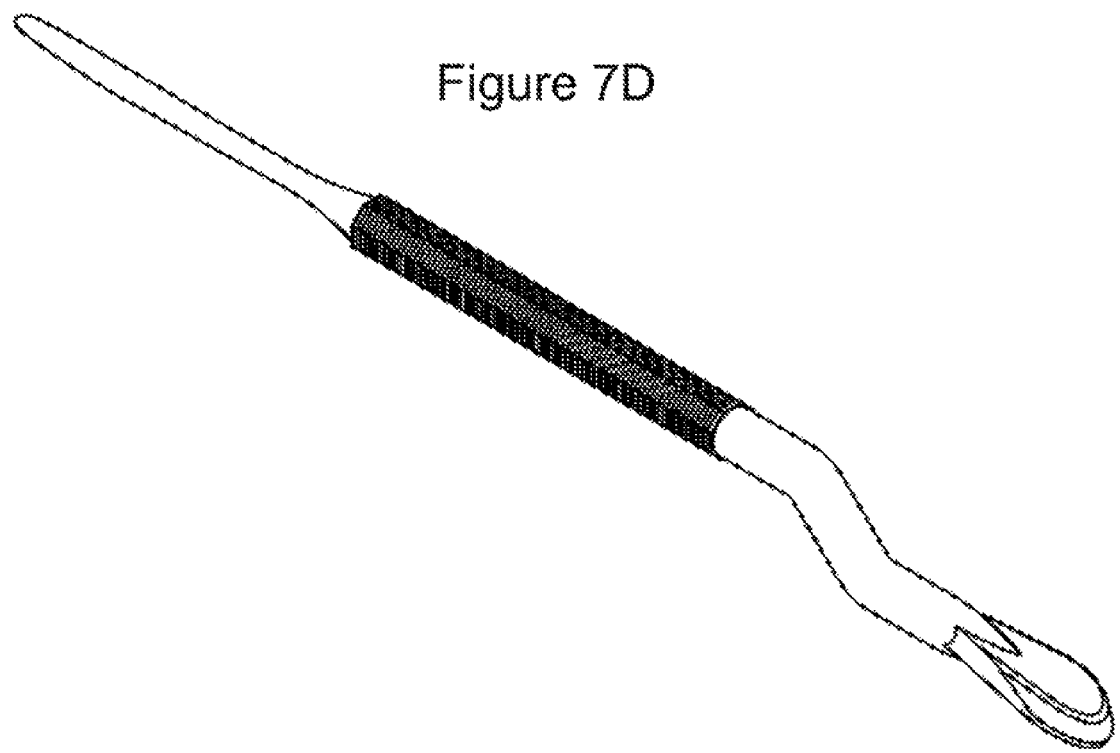
Figure 7E:
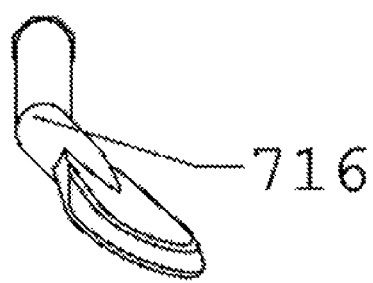
Figure 7F:
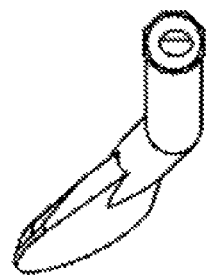

In one embodiment, the neck region may also include a lateral bend positioned at the proximal end of the operational unit, so as to position the operational unit either to the right or the left with respect to the central axis of the handle. As shown in FIG. 7a, the combination tongue and flap retractor 710 includes a bend 716, which may be useful in navigating the instrument on one particular side of the mandible. This design feature allows the Dentist to utilize the instrument in a dramatically less awkward fashion. Furthermore, this design allows the Dentist to reduce or eliminate the need for twisting or turning their torso, upper extremities, and head and neck in an effort to use the instrument. Thus, the risk of injury to the Dentist can also be reduced or eliminated. This embodiment also includes the S-shaped bend 717 in the neck region 715 for better ergonomics and advantages as described herein.

Figure 8A:
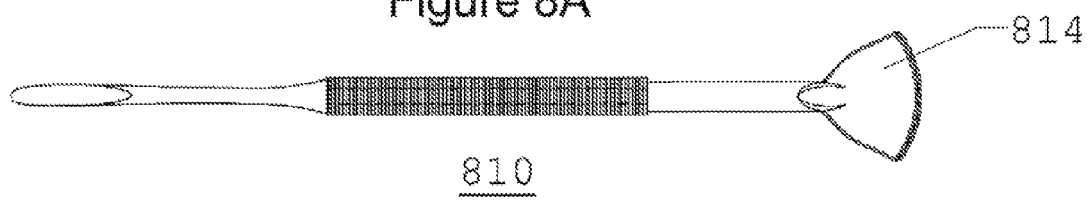
FIG. 8a is a bottom elevation view of a concave tongue retractor with an S-shaped bend in accordance with an embodiment of the present invention.
Figure 8B:
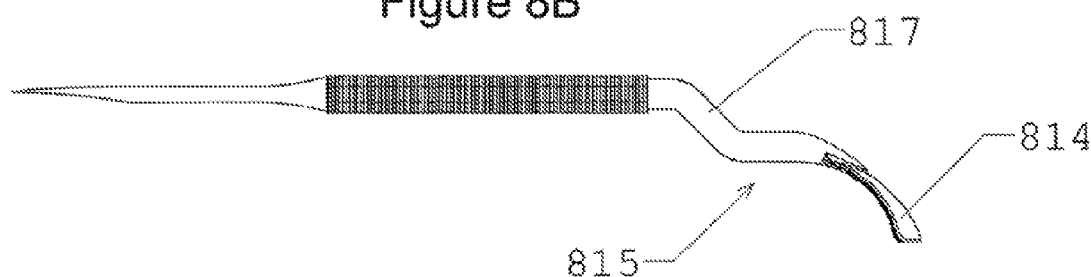
Figure 8C:
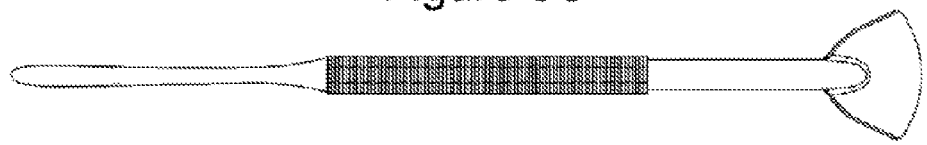
Figure 8D:
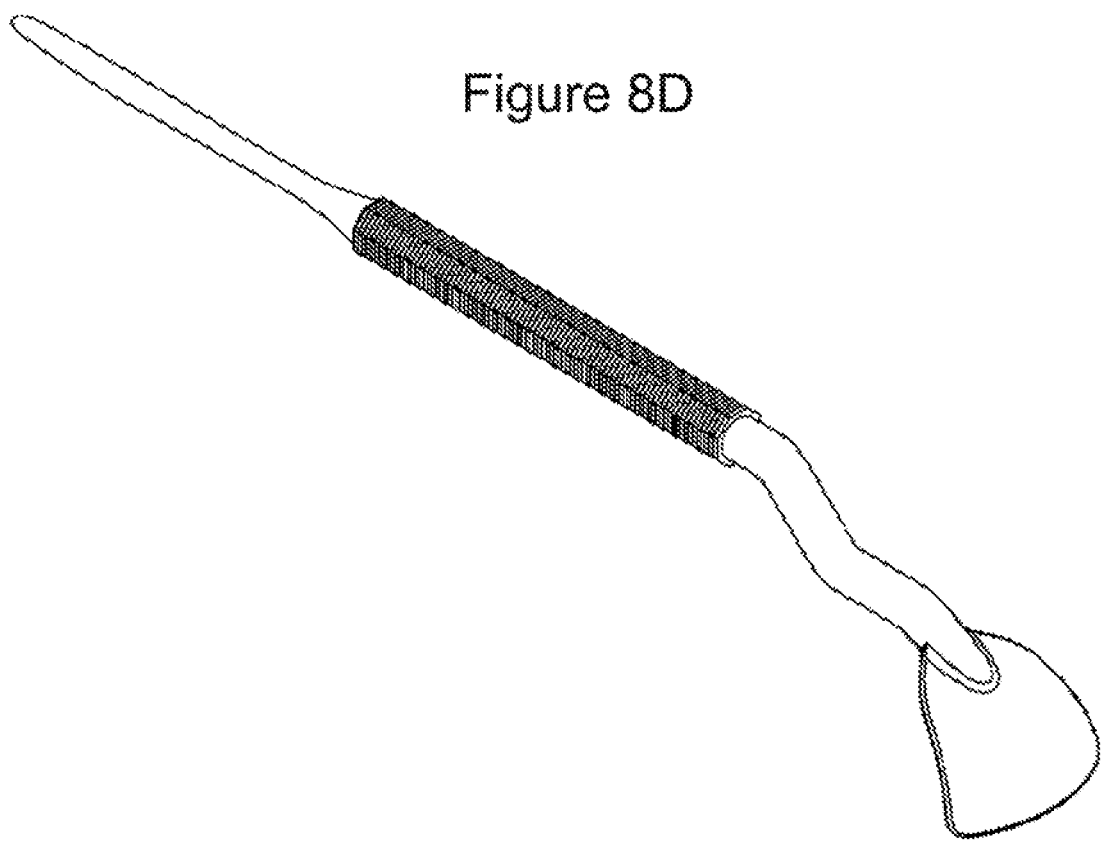
Figure 8E:
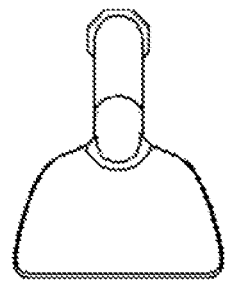
Figure 8F:
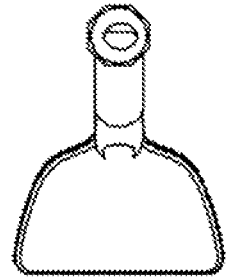

Though the previous embodiments have described tongue and flap retractors in combination, in another embodiment, the features of the tongue retractor disclosed above may be implemented without a flap retractor. FIG. 8a shows a straight concave tongue retractor 810 with a concave design 814 for tongue encapsulation without a flap retractor. The straight concave tongue retractor 810 also includes the S-shaped bend 817 in the neck region 815 for better ergonomics and advantages as described herein.

Figure 9A:
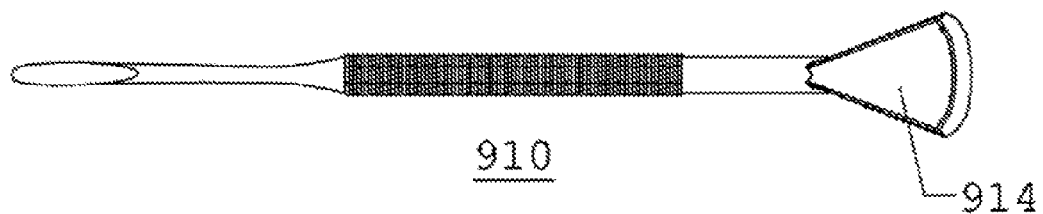
FIG. 9a is a bottom elevation view of a more sharply curved concave tongue retractor with an S-shaped bend in accordance with an embodiment of the present invention.
Figure 9B:
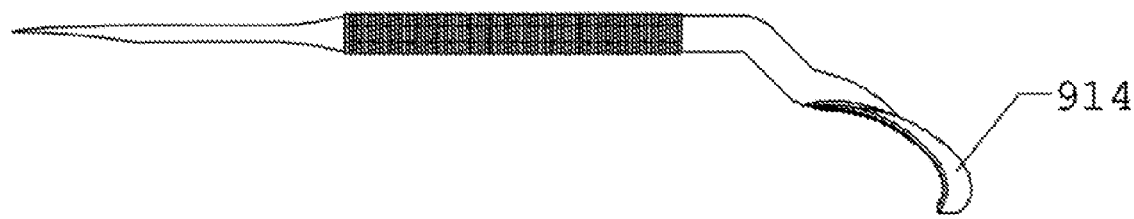
Figure 9C:
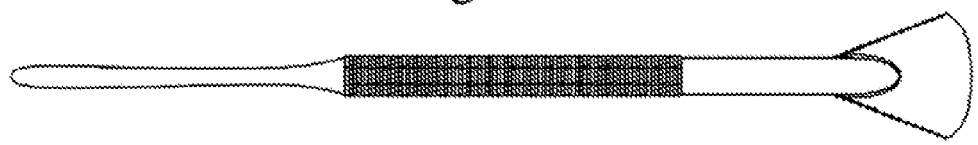
Figure 9D:
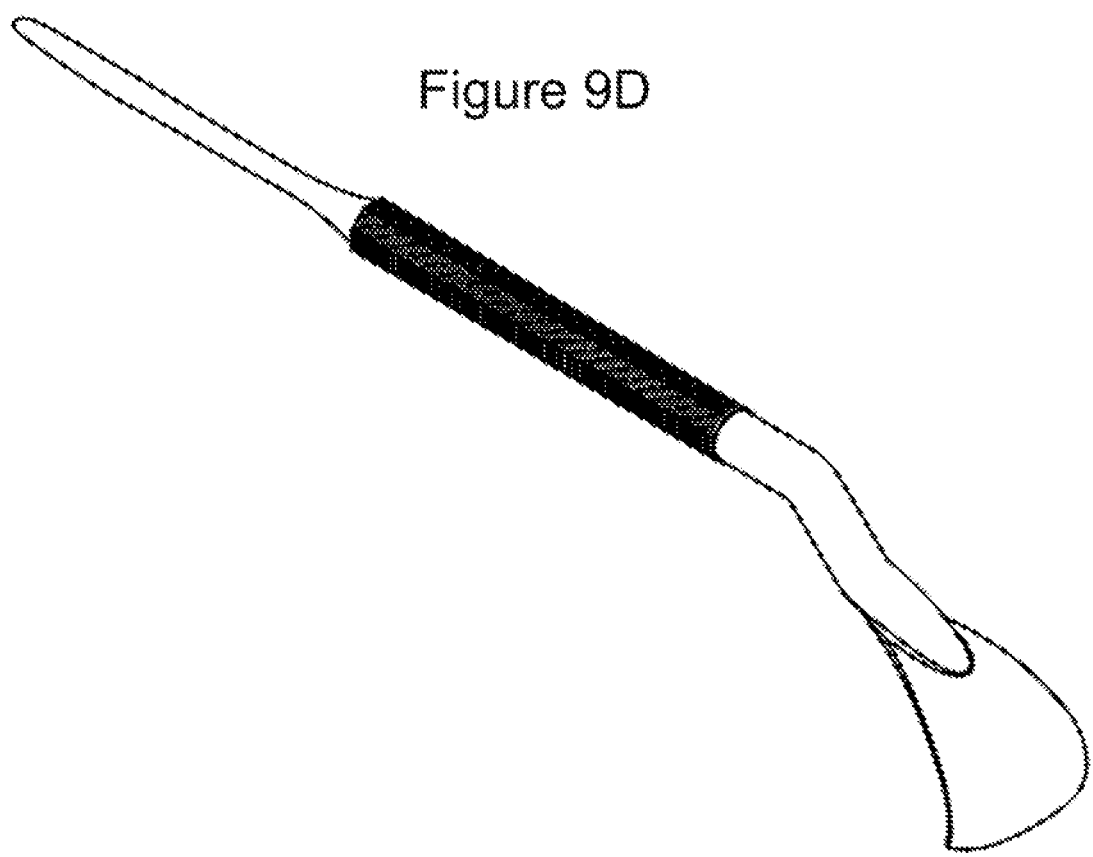
Figure 9E:
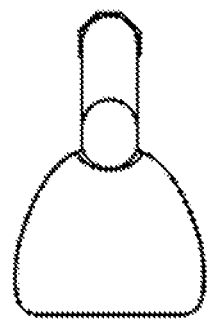
Figure 9F:
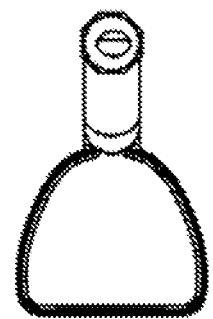

Likewise, FIG. 9a shows a concave tongue retractor 910 similar to the straight concave tongue refractor 810, but with a longer, and more sharply curved tongue retractor 914 for better encapsulation of the tongue. The concave tongue retractor 910 may be formed by sharply curving the distal portion of the tongue retractor 914.

Figure 10A:
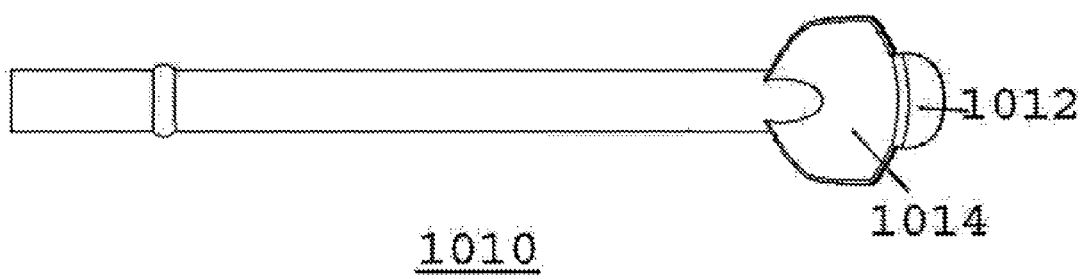
FIG. 10a is a bottom elevation view of a combination concave tongue and flap retractor with an S-shaped bend and a high speed suction device in accordance with an embodiment of the present invention.
Figure 10B:
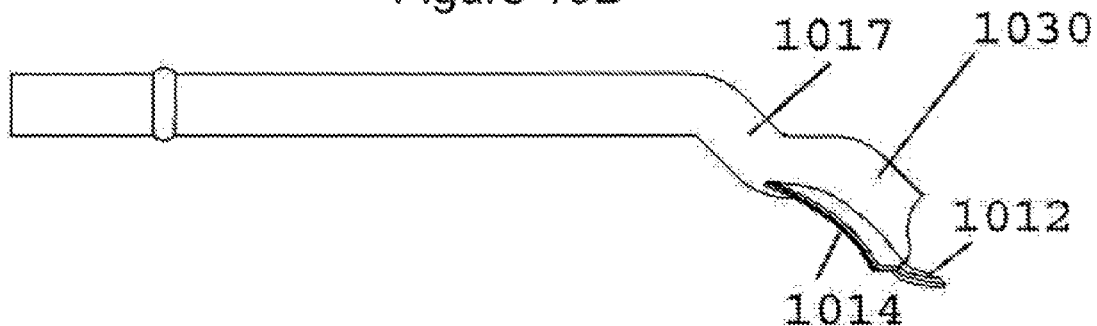
Figure 10C:
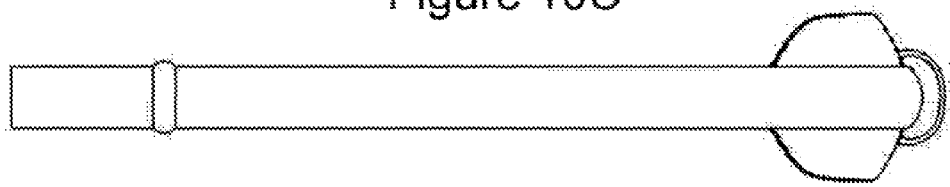
Figure 10D:
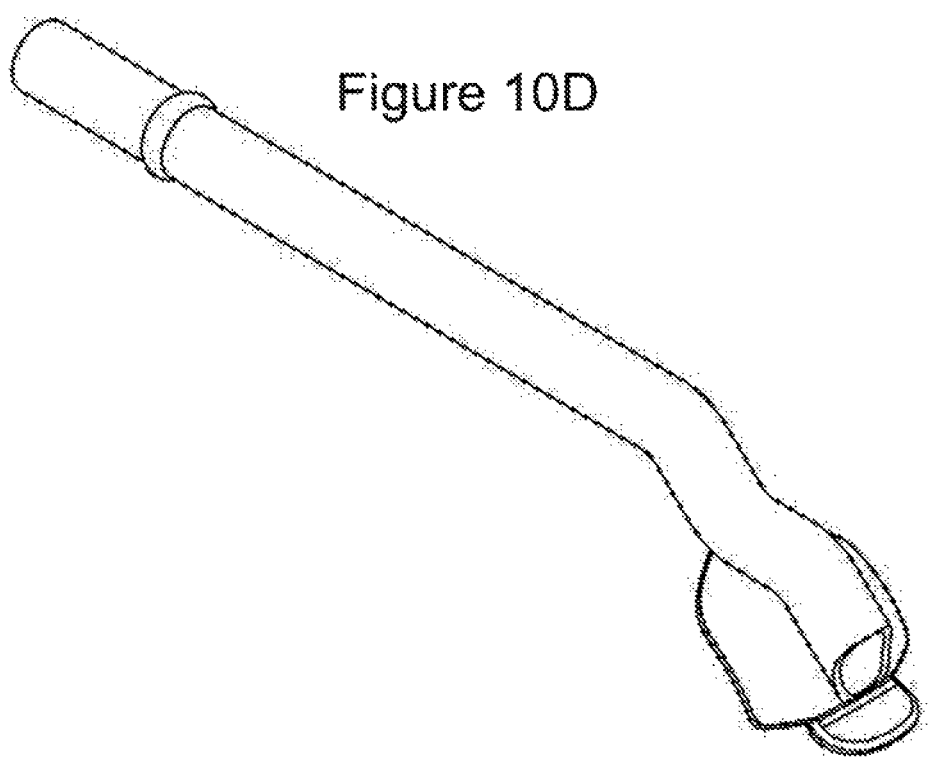
Figure 10E:
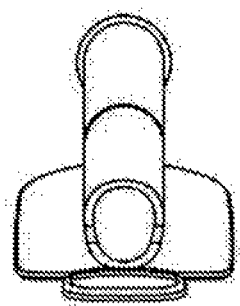
Figure 10F:
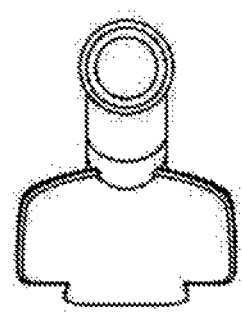

Finally, a high speed suction device may be incorporated in conjunction with any of the instruments disclosed herein. As shown in FIG. 10a, a high speed suction device 1010 includes many of the features described above. For example, the suction device 1010 includes a tongue retractor 1014, and a flap retractor 1012, as well as an S-shaped bend 1017. Furthermore, the suction device 1010 includes a suction shaft 1030 for eliminating fluids such as saliva, water, and blood from the oral cavity. The suction shaft may be in the form of a tube, duct or otherwise hollow body capable of eliminating fluids from the area of operation.

Thus, while there have been shown, described, and pointed out fundamental novel features of the invention as applied to several embodiments, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated.

What is claimed is:

1. A dental retractor, comprising:
   an operational unit having a concave tongue retractor located at a distal end region of said operational unit, a bottom surface of the tongue retractor having orthogonal cross-sections and substantially open sides, each cross-section including a concave-shaped portion, the bottom surface capable of contacting and encapsulating at least a portion of the tongue, the tongue retractor having a top surface opposing the bottom surface;
   a neck connected to said operational unit at a proximal end of said operational unit; and
   a handle connected to said neck at a proximal end of said neck;
   wherein the neck comprises a first portion connected to the handle and angled downward with respect to a longitudinal axis of the handle, and a second portion connected to the first portion and the operational unit and angled upward with respect to a longitudinal axis of the first portion, a distal end of the second portion downwardly offset from the longitudinal axis of the handle, the second portion angled downward with respect to the longitudinal axis of the handle.

2. The dental retractor of claim 1, wherein the neck further comprises a lateral bend to laterally offset the operational unit to the left or to right with respect to the longitudinal axis of the handle.

3. The dental retractor of claim 1, wherein the dental retractor is a unitary structure.

4. The dental retractor of claim 1, wherein the dental retractor is formed of at least two removably connected segments.

5. The dental retractor of claim 1, further comprising a suction shaft.

6. The dental retractor of claim 1, wherein the handle includes a faceted cross sectional shape.

7. A dental tool, comprising:
   a handle;
   a tongue retractor coupled to the handle at a first end of the tongue retractor, the tongue retractor comprising a bottom surface capable of contacting and encapsulating at least a portion of a tongue and a convex top surface, the bottom surface having orthogonal cross-sections and substantially open sides, each cross-section including a concave-shaped portion; and
   an S-shaped neck portion coupling the tongue retractor to the handle and configured to downwardly offset a proximal end of the tongue retractor with respect to a longitudinal axis of the handle, a distal end of the S-shaped neck portion angled downward with respect to the longitudinal axis of the handle.

8. The dental tool of claim 7, wherein the neck portion further comprises a lateral bend.

9. The dental tool of claim 7, wherein the dental tool is a unitary structure.

10. The dental tool of claim 7, wherein the dental tool is formed of at least two removably connected segments.

11. The dental tool of claim 7, further comprising a suction shaft.

12. The dental tool of claim 7, wherein the handle includes a faceted cross sectional shape.

13. A dental tool, comprising:
a handle;
a neck connected to the handle, the neck comprising:
   a first portion connected to a distal end of the handle and extending distally along a direction parallel to the handle;
   a second portion angled downward with respect to a longitudinal axis of the first portion, a proximal end of the second portion connected to a distal end of the first portion; and
   a third portion angled upward with respect to a longitudinal axis of the second portion and angled downward with respect to a longitudinal axis of the handle, a proximal end of the third portion connected to a distal end of the second portion, the distal end of the third portion downwardly offset from the longitudinal axis of the handle; and
a tongue retractor connected to a distal end of the third portion of the neck, the tongue retractor comprising a bottom surface capable of contacting and encapsulating at least a portion of a tongue and an opposing top surface, the bottom surface having orthogonal cross-sections and substantially open sides, each cross-section including a concave-shaped portion.

14. The dental tool of claim 13, wherein the neck further comprises a lateral bend to laterally offset the tongue retractor to the left or to right with respect to the longitudinal axis of the handle.

15. The dental tool of claim 13, wherein the dental tool is a unitary structure.

16. The dental tool of claim 13, wherein the dental tool is formed of at least two removably connected segments.

17. The dental tool of claim 13, further comprising a suction shaft.

18. The dental tool of claim 13, wherein the handle includes a faceted cross sectional shape.

19. A dental retractor, comprising:
a neck connected to an operational unit at a proximal end of said operational unit; and
a handle connected to said neck at a proximal end of said neck;
said operational unit having a concave tongue retractor located at a distal end region of said operational unit, a bottom surface of the tongue retractor having orthogonal cross-sections and substantially open sides, each cross-section including a concave-shaped portion, the bottom surface capable of contacting and encapsulating at least a portion of the tongue, the tongue retractor further having a terminal tip which is located proximally closer to the handle portion of the retractor than an apex of the concave-shaped portion of at least one of the cross-sections, the terminal tip extending from one of the open sides to the other of the open sides;
wherein the neck comprises a first portion connected to the handle and angled downward with respect to a longitudinal axis of the handle, and a second portion connected to the first portion and the operational unit and angled upward with respect to a longitudinal axis of the first portion, a distal end of the second portion downwardly offset from the longitudinal axis of the handle.

20. The dental retractor of claim 19, wherein the neck further comprises a lateral bend to laterally offset the operational unit to the left or to right with respect to the longitudinal axis of the handle.

21. The dental retractor of claim 19, further comprising a suction shaft.

22. A dental tool, comprising:
a handle;
a tongue retractor coupled to the handle at a first end of the tongue retractor, the tongue retractor comprising a bottom surface capable of contacting and encapsulating at least a portion of a tongue and a convex top surface, the bottom surface having orthogonal cross-sections and substantially open sides, each cross-section including a concave-shaped portion, the tongue retractor further comprising a terminal tip which is located proximally inward with respect to an apex of the convex top surface of the tongue retractor and curved back towards the handle, the terminal tip extending from one of the open sides to the other of the open sides; and
an S-shaped neck portion coupling the tongue retractor to the handle and configured to downwardly offset a proximal end of the tongue retractor with respect to a longitudinal axis of the handle.

23. The dental tool of claim 22, wherein the neck portion further comprises a lateral bend.

24. The dental tool of claim 22, further comprising a suction shaft.

25. A dental tool, comprising:
a handle;
a neck connected to the handle, the neck comprising:
   a first portion connected to a distal end of the handle and extending distally along a direction parallel to the handle;
   a second portion angled downward with respect to a longitudinal axis of the first portion, a proximal end of the second portion connected to a distal end of the first portion; and
   a third portion angled upward with respect to a longitudinal axis of the second portion, a proximal end of the third portion connected to a distal end of the second portion, the distal end of the third portion downwardly offset from the longitudinal axis of the handle; and
a tongue retractor connected to a distal end of the third portion of the neck, the tongue retractor comprising a bottom surface capable of contacting and encapsulating at least a portion of a tongue and an opposing top surface, the bottom surface having orthogonal cross-sections and substantially open sides, each cross-section including a concave-shaped portion, the tongue retractor further having a terminal tip which is located proximally closer to the handle than an apex of the concave-shaped portion of at least one of the cross-sections.

26. The dental tool of claim 25, wherein the neck portion further comprises a lateral bend.

27. The dental tool of claim 25, further comprising a suction shaft.

28. The dental retractor of claim 1, wherein the bottom surface is smoothly continuous across the open sides.

29. The dental tool of claim 7, wherein the bottom surface is smoothly continuous across the open sides.

30. The dental tool of claim 13, wherein the bottom surface is smoothly continuous across the open sides.

31. The dental retractor of claim 19, wherein the bottom surface is smoothly continuous across the open sides.

32. The dental tool of claim 22, wherein the bottom surface is smoothly continuous across the open sides.

33. The dental tool of claim 25, wherein the bottom surface is smoothly continuous across the open sides.

\* \* \* \* \*